(12) United States Patent
Kanemaru et al.

(10) Patent No.: US 10,814,095 B2
(45) Date of Patent: Oct. 27, 2020

(54) APPARATUS, SOUND DATA GENERATION METHOD, AND NON-TRANSITORY COMPUTER READABLE STORAGE MEDIUM

(71) Applicant: HITACHI, LTD., Tokyo (JP)

(72) Inventors: Takashi Kanemaru, Tokyo (JP); Nobuhiro Fukuda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 420 days.

(21) Appl. No.: 15/888,963

(22) Filed: Feb. 5, 2018

(65) Prior Publication Data

US 2018/0221621 A1 Aug. 9, 2018

(30) Foreign Application Priority Data

Feb. 6, 2017 (JP) ................. 2017-019369

(51) Int. Cl.
*A61M 21/02* (2006.01)
*G06F 3/16* (2006.01)
*G06F 3/01* (2006.01)
*H04N 21/44* (2011.01)
*H04N 21/414* (2011.01)
(Continued)

(52) U.S. Cl.
CPC .......... *A61M 21/02* (2013.01); *G06F 1/1694* (2013.01); *G06F 3/012* (2013.01); *G06F 3/165* (2013.01); *H04N 21/41422* (2013.01); *H04N 21/439* (2013.01); *H04N 21/44008* (2013.01); *H04N 21/44218* (2013.01); *A61M 2021/005* (2013.01); *A61M 2021/0027* (2013.01); *A61M 2205/332* (2013.01); *A61M 2205/3306* (2013.01);
(Continued)

(58) Field of Classification Search
CPC .......... A61M 21/00; G06F 3/01; G06F 3/012; G06F 3/165
USPC ...................................... 600/26–28
See application file for complete search history.

(56) References Cited

U.S. PATENT DOCUMENTS

2016/0228771 A1 8/2016 Watson

FOREIGN PATENT DOCUMENTS

JP 2006-288665 A 10/2006
JP 2008-230575 A 10/2008
(Continued)

OTHER PUBLICATIONS

Japanese Office Action dated Jan. 7, 2020 for the Japanese Patent Application No. 2017-019369.

*Primary Examiner* — John P Lacyk
(74) *Attorney, Agent, or Firm* — Volpe and Koenig

(57) ABSTRACT

An apparatus includes a first acquisition unit acquiring head position information indicating a user's head movement, a second acquisition unit acquiring stimulus information relating to a stimulus input to visual and vestibular sense. A generation unit that generates sound data of sound effect generating movement of a body which reduces sickness based on the head position information and the stimulus information, and calculates a variation amount of the user's head position based on the head position information, calculates an estimation amount for a magnitude of the stimulus input to at least any one of visual and vestibular sense based on the stimulus information, calculates sickness feeling intensity based on the variation amount and the estimation amount, calculates a reduction amount for calculating a feature amount of the sound data based on the sickness feeling intensity, and calculates a feature amount of the sound data based on the reduction amount.

15 Claims, 9 Drawing Sheets

(51) Int. Cl.
*H04N 21/439* (2011.01)
*G06F 1/16* (2006.01)
*H04N 21/442* (2011.01)
*A61M 21/00* (2006.01)

(52) U.S. Cl.
CPC ... *A61M 2205/502* (2013.01); *A61M 2205/52* (2013.01); *A61M 2230/63* (2013.01)

(56) References Cited

FOREIGN PATENT DOCUMENTS

| | | |
|---|---|---|
| JP | 2011-020539 A | 2/2011 |
| JP | 2015-182755 A | 10/2015 |

[Fig. 1]
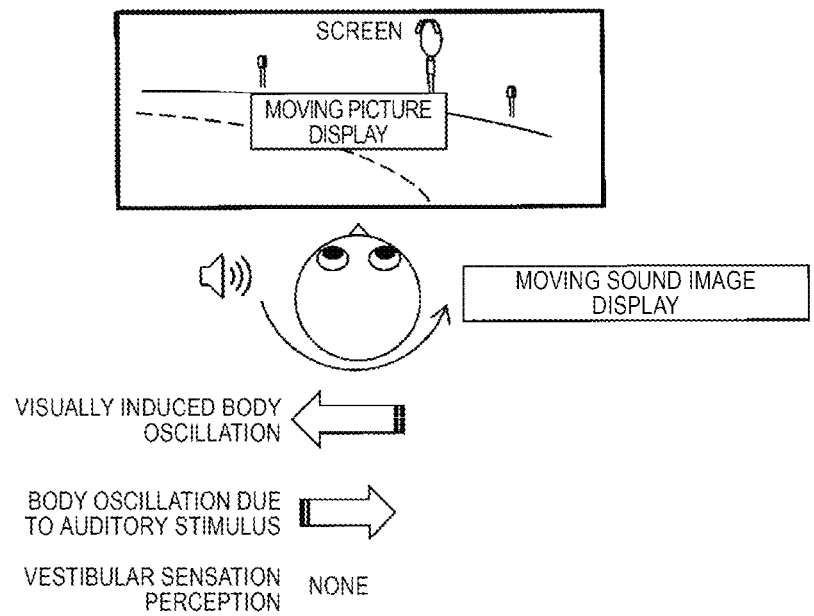
[Fig. 2]
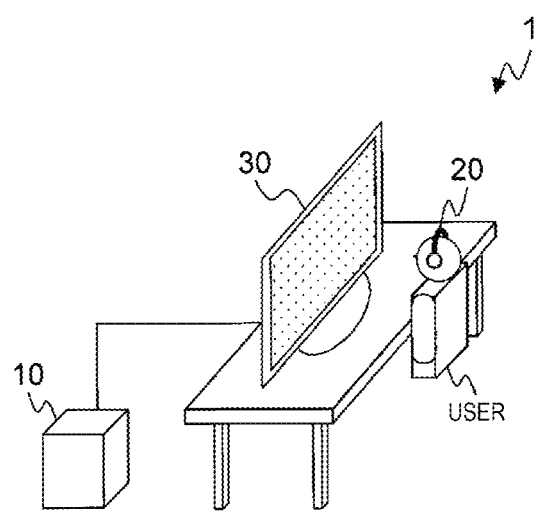

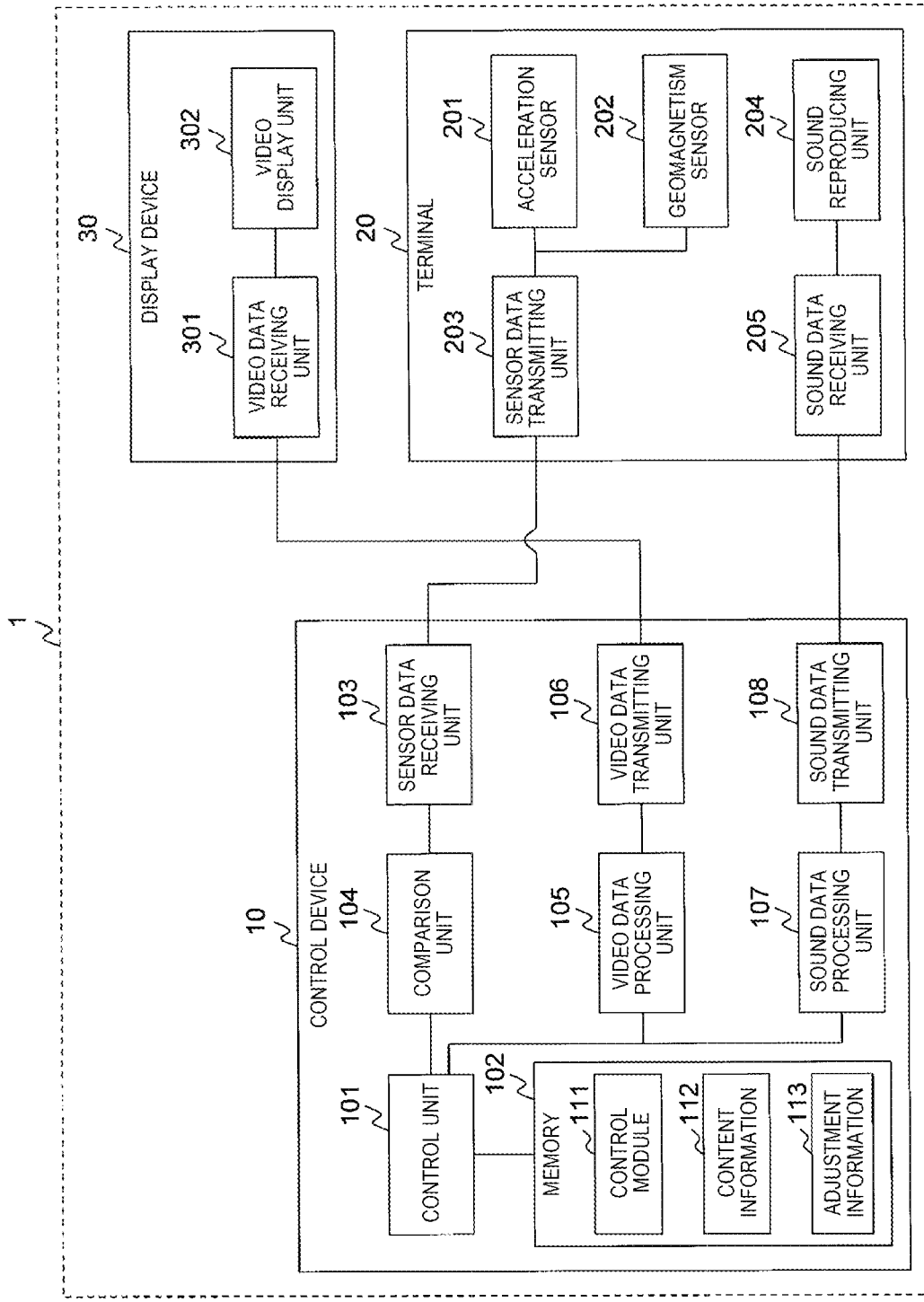
[Fig. 3]

[Fig. 4]

113
ADJUSTMENT INFORMATION

400

| AGES (401) | MAXIMUM AUDIBLE FREQUENCY (Hz) (402) |
|---|---|
| 10s | 20,000 |
| 20s | 16,000 |
| 30s | 15,000 |
| 40s | 14,000 |
| 50s | 12,000 |
| 60s | 10,000 |

[Fig. 5]

500
USER INFORMATION REGISTRATION SCREEN

NAME [_____] 501

AGE [10 - 19 ▼] 502

SEX ( ● ) MALE  ( ○ ) FEMALE   503

SICKNESS FREQUENCY [EVER-SICK ▼] 504

[ REGISTRATION ] 505   [ CANCEL ] 506

[Fig. 6]
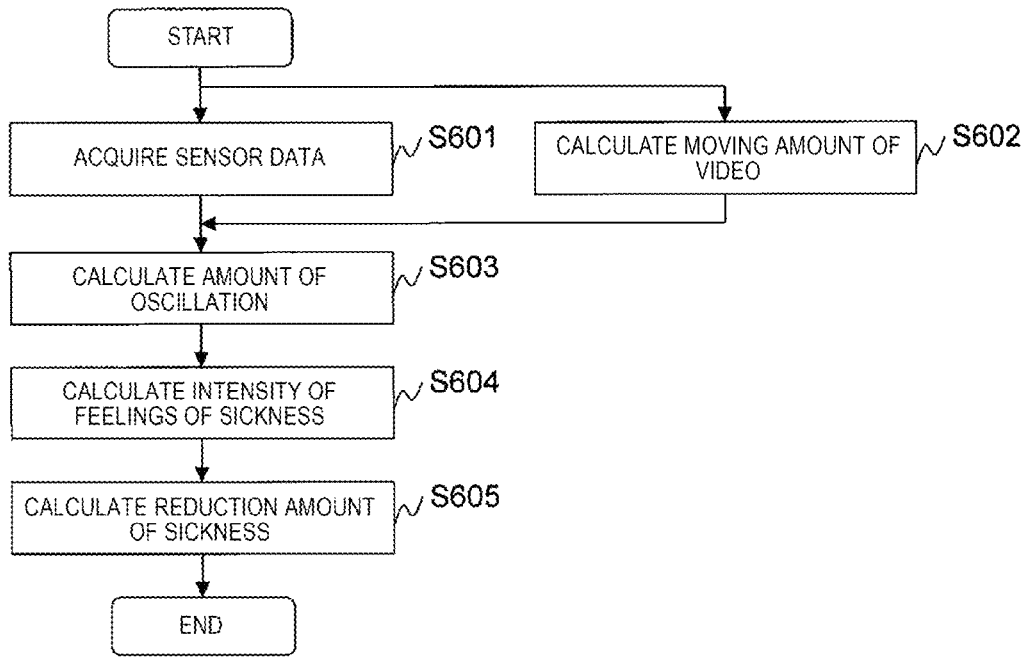
[Fig. 7]
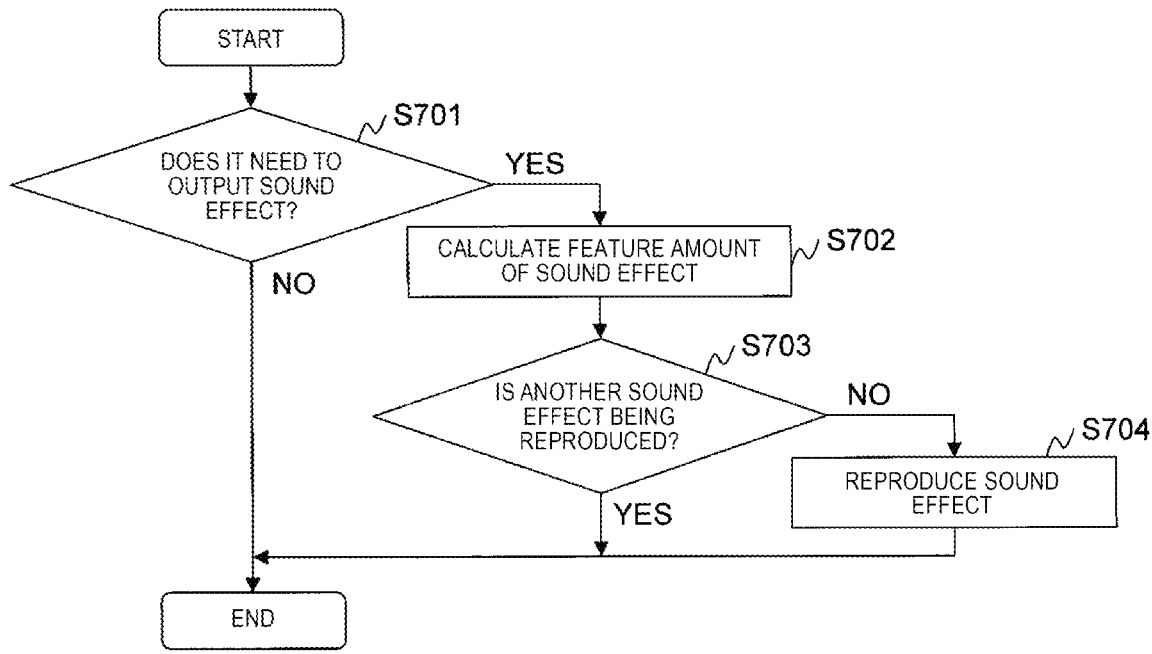

[Fig. 8A]
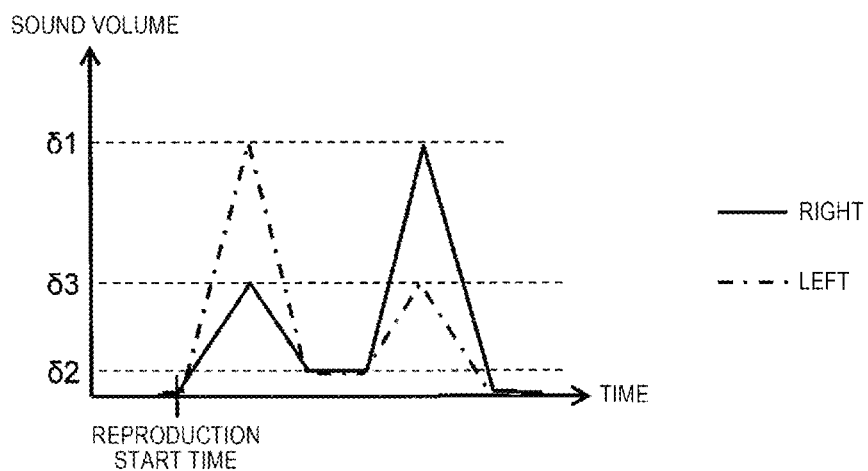
[Fig. 8B]
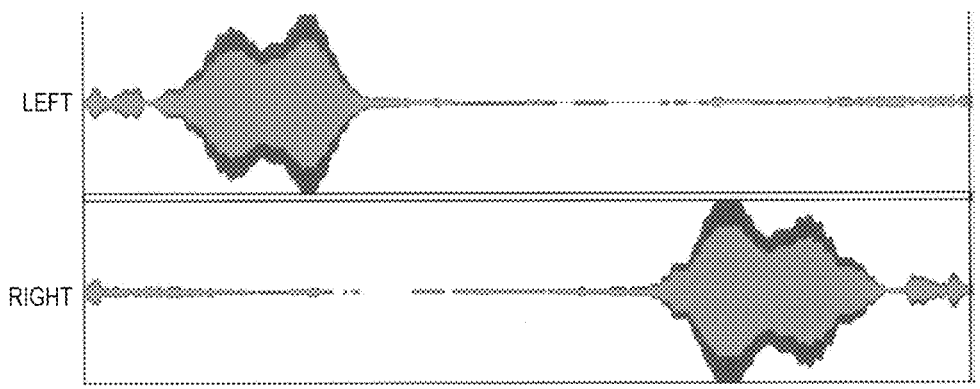
[Fig. 9]
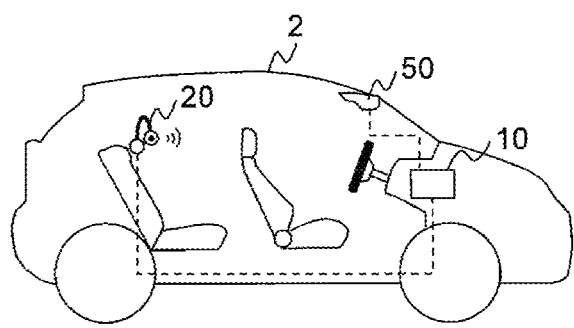

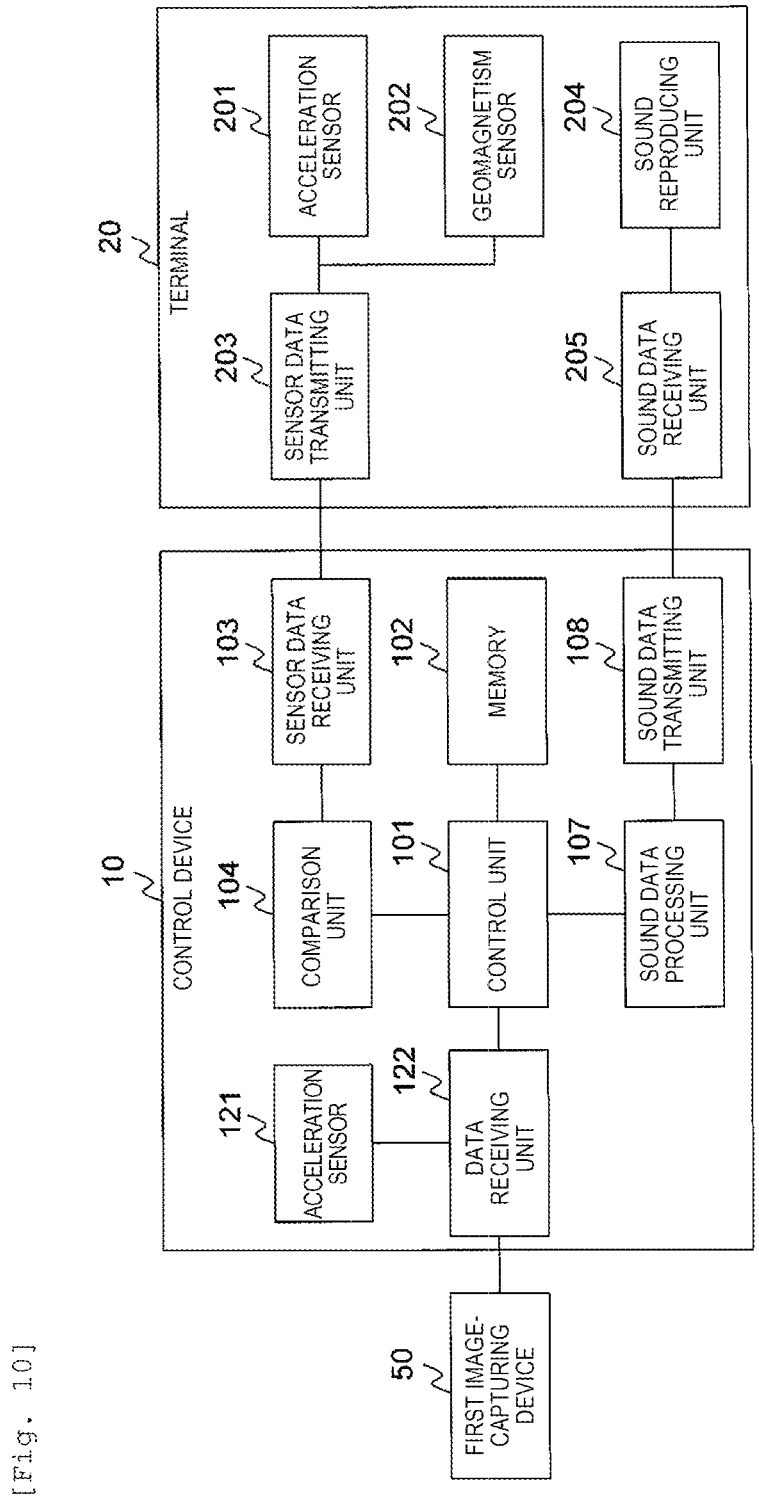
[Fig. 10]

[Fig. 11]
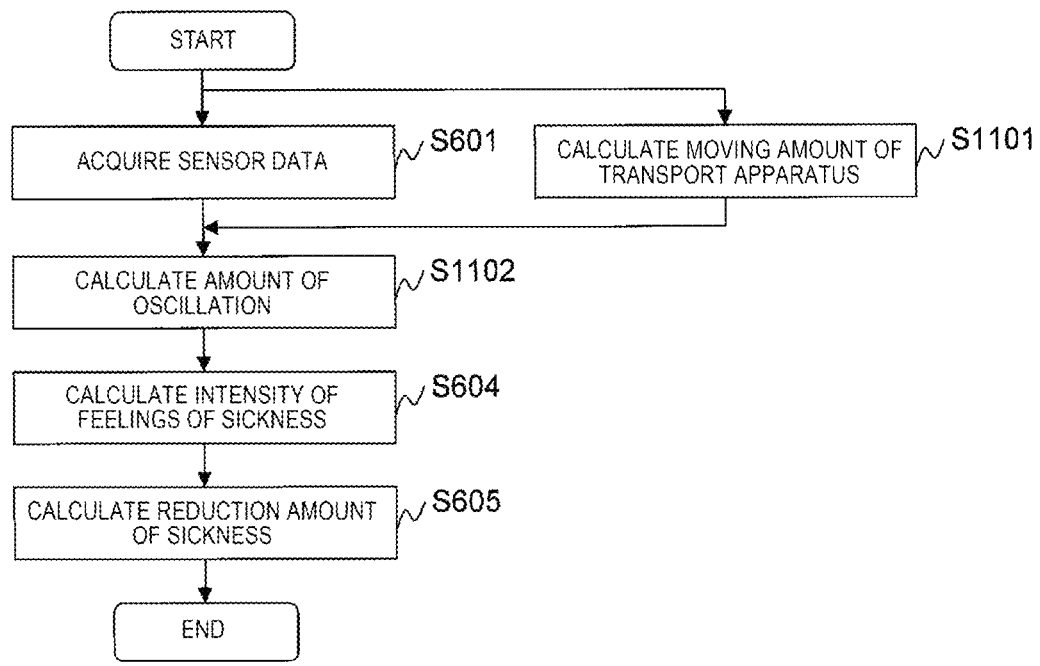
[Fig. 12]
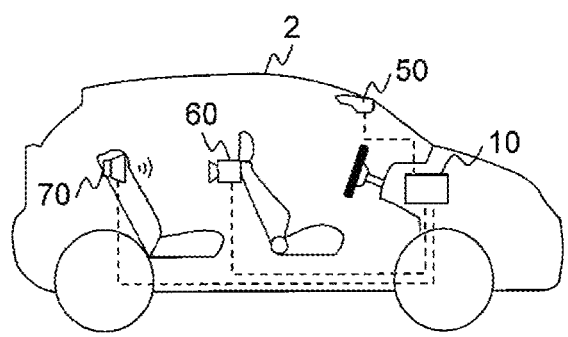

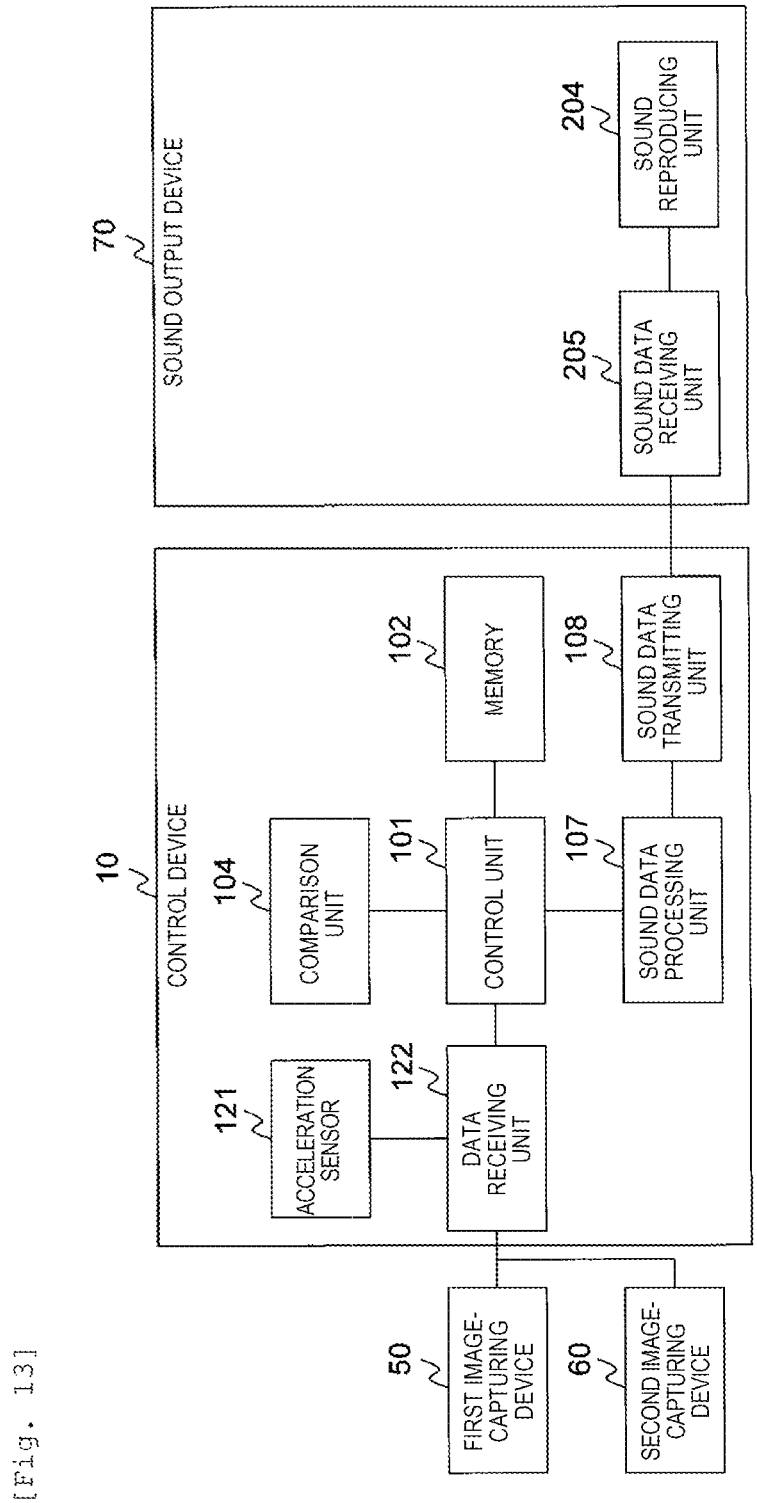
[Fig. 13]

[Fig. 14]
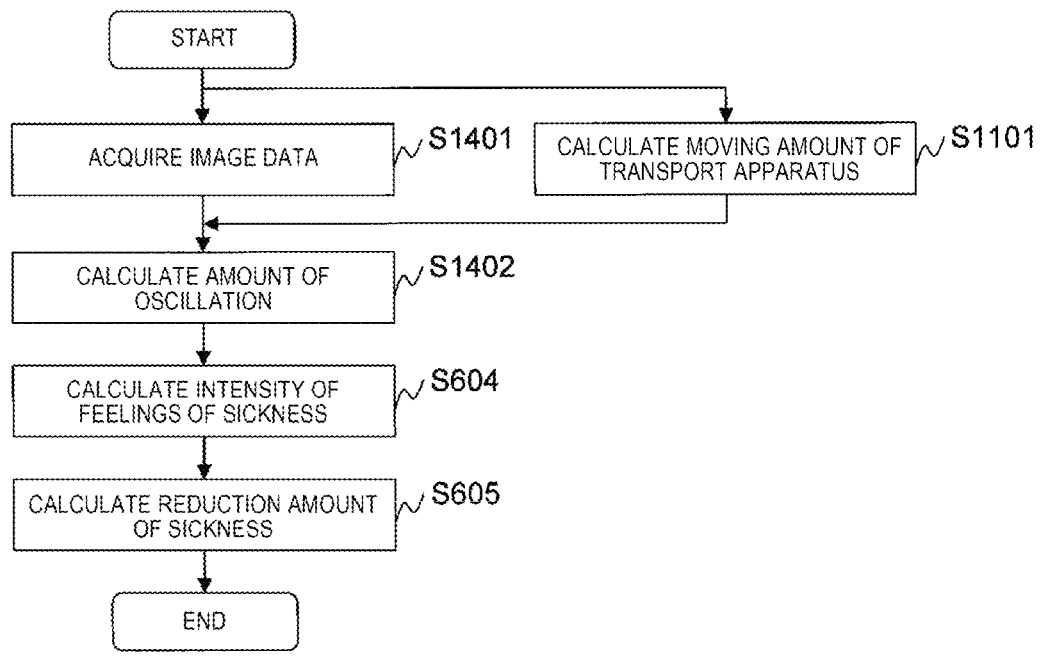

APPARATUS, SOUND DATA GENERATION METHOD, AND NON-TRANSITORY COMPUTER READABLE STORAGE MEDIUM

CLAIM OF PRIORITY

The present application claims priority from Japanese patent application JP 2017-019369 filed on Feb. 6, 2017, the content of which is hereby incorporated by reference into this application.

TECHNICAL FIELD

The present invention relates to an apparatus that outputs sound effect reducing sickness of a user, a method, and a non-transitory computer readable storage medium.

BACKGROUND ART

There is reduction of sickness as a problem to be solved for improving comfort while getting on a transport apparatus or during viewing of video.

In an occurrence mechanism of an oscillation disease (motion sickness) among sicknesses described above, the sensory conflict theory in which discrepancy between stimuli input to a plurality of sense organs is regarded as a main cause is known as a widely-accepted theory. Although visually induced motion sickness basically occurs in a state where the body is being kept stationary and is different from an oscillation disease accompanied by variation and swing of the body in the occurrence environment, it is considered that discrepancy between input stimuli is the main cause, similar to the oscillation disease.

As solutions for reducing and eliminating such sickness, for example, technologies such as PTL 1 and PTL 2 are known.

In PTL 1, a technology in which "the video control means 14 combines message video on video generated by the video generation means 11 for a fixed period of time according to the traveling condition of the vehicle detected by the traveling condition detection means 12 that detects the traveling condition of the vehicle and the vehicle condition detected by the vehicle condition detection means 13 that detects the condition within the vehicle and thus, an occupant is able to be allowed to grasp and predict the present motion and the next motion of a vehicle simultaneously while allowing the occupant seated in the rear seat to view video of a television or the like in the vehicle and a risk and burden on the occupant seated in the rear seat is reduced" is disclosed.

In PTL 2, a technology in which "the current command value inputting unit 200 detects shaking of the ship and oscillation of the user by the inclination sensors 51-1 and 51-2 in the oscillation feeling suppressing apparatus. The output inclination 51-1a of the inclination sensor 51-1 is used as a source signal to generate the current command value 10. According to the current command value 10, the electric stimulating apparatus 100 generates the current between electrodes to give acceleration feeling in a direction of canceling shaking of the ship to the user. The oscillation feeling perceived by the user is suppressed." is disclosed.

CITATION LIST

Patent Literature

PTL 1: JP-A-2011-20539
PTL 2: JP-A-2006-288665

SUMMARY OF INVENTION

Technical Problem

In a case of the technology of PTL 1, the occupant needs to perform the action or the like for eliminating sickness based on message video. In the technology described in PTL 2, the usable time is short by taking into account an influence to a human body for allowing the current flow directly to the human body, and the introduction cost of the apparatus is high since the apparatus is special.

The present invention has an object to provide an apparatus that implements reduction of sickness in matching with the degree of sickness of a user without giving a burden on the user, a method, and a program.

Solution to Problem

A representative example of the invention disclosed in the present specification is as follows. That is, there is provided an apparatus that reduces sickness of a user, and the apparatus includes a first acquisition unit that acquires head position information indicating movement of a head of the user, a second acquisition unit that acquires stimulus information relating to a stimulus input to a visual sense and a vestibular sense, and a generation unit that generates sound data of sound effect generating movement of a body which reduces sickness based on the head position information and the stimulus information, and the generation unit calculates a variation amount of a position of a head of the user based on the head position information, calculates an estimation amount for estimating a magnitude of the stimulus input to at least any one of the visual sense and the vestibular sense based on the stimulus information, calculates sickness feeling intensity indicating intensity of sickness feeling of the user based on the variation amount of the position of the head of the user and the estimation amount, calculates a reduction amount for calculating a feature amount of the sound data based on the sickness feeling intensity, and calculates a feature amount of sound data based on the reduction amount to generate the sound data.

Advantageous Effects of Invention

According to the present invention, it is possible to implement reduction of sickness in matching with the degree of sickness of a user without giving a burden on the user by using sound effect that generates movement of the body which reduces the sickness. Problems to be solved, configurations, and effects other than those described above become clear from the following description of examples.

BRIEF DESCRIPTION OF DRAWINGS

FIG. 1 is a diagram illustrating a concept of the present invention.

FIG. 2 is a diagram illustrating a configuration of a sound generation device of Example 1.

FIG. 3 is a diagram illustrating the configuration of the sound generation device of Example 1.

FIG. 4 is a diagram illustrating an example of a hardware configuration and software configuration of the sound generation device of Example 1.

FIG. 5 is a diagram illustrating an example of adjustment information of Example 1 and is a diagram illustrating an example of a personal information input screen of Example 1.

FIG. 6 is a diagram for explaining processing executed by a control device of Example 1.

FIG. 7 is a diagram for explaining processing executed by the control device of Example 1.

FIG. 8A is a diagram illustrating an example of sound effect reproduced by a terminal of Example 1.

FIG. 8B is a diagram illustrating an example of sound effect reproduced by the terminal of Example 1.

FIG. 9 is a diagram illustrating a configuration of a sound generation device mounted on a transport apparatus of Example 2.

FIG. 10 is a diagram illustrating an example of a hardware configuration and software configuration of a sound generation device of Example 2.

FIG. 11 is a diagram for explaining processing executed by a control device of Example 2.

FIG. 12 is a diagram illustrating a configuration of a sound generation device mounted on a transport apparatus of Example 3.

FIG. 13 is a diagram illustrating an example of a hardware configuration and software configuration of a sound generation device of Example 3.

FIG. 14 is a diagram for explaining processing executed by a control device of Example 3.

DESCRIPTION OF EMBODIMENTS

In the following, embodiments of the present invention will be described using the drawings. In the following description, the same reference numerals are given to the same configurations throughout all drawings and redundant description thereof will be omitted.

FIG. 1 is a diagram illustrating a concept of the present invention.

Currently, the sensory conflict theory is considered most appropriate as an occurrence mechanism of sickness. In the sensory conflict theory, discrepancy between perception by visual sense and perception by vestibular sense is considered the main cause of sickness.

As illustrated in FIG. 1, in a case where the user who is seated on a seat views video projected on a screen, the user passively enjoys a visual stimulus without actively moving the head. For that reason, matters that the body is moving in the left direction are perceived by visual sense. However, matters that the body remains stationary are perceived by vestibular sense. The discrepancy between perceptions described above is considered the cause of sickness. For example, the research that investigates correlation between the magnitude of visual guidance body motion and a subjective sickness symptom is known.

Matters that the body motion can be guided by an auditory stimulus are pointed out by the research and experiment. Specifically, sense that the user himself/herself is moving can be generated by a phase and sound volume of sound, frequency change, and gradient using direction perception of auditory sense.

In the present invention, in order to eliminate discrepancy in perception, which is the main cause of sickness, between visual sense and vestibular sense, the auditory stimulus generating movement of the body is input to the user so as to reduce sickness. In FIG. 1, the auditory stimulus suppressing movement in the left direction is given to the user to reduce sickness.

Example 1

FIG. 2 is a diagram illustrating a configuration of a sound generation device 1 of Example 1.

In FIG. 2, the sound generation device 1 which is used in such a way that the user is seated so as to be opposed to a display device 30 is illustrated. For example, a use case in which a desired content is selected from among contents such as a moving picture managed by a control device 10 to view video is considered.

The sound generation device 1 is configured with the control device 10, a terminal 20, and the display device 30. The terminal 20 and the display device 30 are connected with the control device 10 wirelessly or in a wired manner.

The control device 10 displays video that gives a stimulus to visual sense of the user by controlling the display device 30 and reproduces sound that gives a stimulus to auditory sense of the user by controlling the terminal 20. The control device 10 controls generating and outputting of sound data of sound that reduces sickness of the user. The control device 10 is considered, for example, a typical computer.

The terminal 20 outputs sound based on sound data and detects a face direction of the user. In the present embodiment, the terminal 20 is worn on the head of the user. The terminal 20 is considered, for example, a headphone. As sound data, sound data of sound (music, voice, or the like) accompanied by displaying of video data and sound data of sound effect reducing sickness of the user are included. In the following description, sound effect reducing sickness of the user is simply described as sound effect.

The display device 30 displays video based on video data. The display device 30 is considered, for example, a projector, a monitor, and the like.

In a case where a plurality of video is projected or displayed at one time, the sound generation device 1 may include the plurality of display devices 30. In this case, the plurality of display devices 30 are connected with the control device 10 and display video in synchronization or asynchronization with other display devices 30.

FIG. 3 is a diagram illustrating an example of a hardware configuration and software configuration of the sound generation device 1 of Example 1.

The control device 10 includes a control unit 101, a memory 102, a sensor data receiving unit 103, a comparison unit 104, a video data processing unit 105, a video data transmitting unit 106, a sound data processing unit 107, and a sound data transmitting unit 108. The control device 10 may include an internal storage device such as a HDD or a SSD.

The control unit 101 is an operation device such as a processor that controls respective configurations within the control device 10. The control unit 101 executes processing according to a program stored in the memory 102 so as to be operated as a module that implements a specific function. In the following description, in a case where processing is explained by using the module as a subject, it is indicated that the control unit 101 executes a program implementing the module.

The memory 102 stores a program executed by hardware such as the control unit 101 and information used by the program. The memory 102 includes a work area temporarily used by the program.

The memory 102 of the present embodiment stores the program implementing a control module 111 and stores content information 112 and adjustment information 113. The control module 111 controls the entirety of the control device 10. The content information 112 is information relating to video to be displayed and sound accompanied by the video. The content information 112 includes video data and sound data. The adjustment information 113 is information used in a case where a feature amount of sound effect is corrected.

Although not illustrated, the memory 102 may store user information for managing information relating to individuality of the user. User information includes an entry configured with personal information (name, age, sex, or the like) of a user, tolerance for sickness of the user, use history of the sound generation device 1, and the like.

The program and information stored in the memory 102 may also be stored in the internal storage device. In this case, the control unit 101 reads the program and information from the internal storage device, loads the program and information onto the memory 102, and executes the program stored in the memory 102.

The sensor data receiving unit 103 receive sensor data transmitted by the terminal 20 and outputs the sensor data to the comparison unit 104. Sensor data to be received includes a value specifying a position, a moving direction, a moving speed, and the like of the head of the user.

The comparison unit 104 calculates a physical amount indicating oscillation of the head of the user using sensor data input from the sensor data receiving unit 103 and compares the physical amount with a physical amount relating to reproduced video to calculate a quantitative value for evaluating the intensity of feelings of sickness (degree of sickness) of the user. In the following description, the quantitative value for evaluating the intensity of feelings of sickness of the user is also described as sickness feeling intensity.

The comparison unit 104 calculates a physical amount for determining a feature amount of sound effect based on sickness feeling intensity. In the present embodiment, the physical amount for determining the feature amount of sound effect based on sickness feeling intensity is also described as a reduction amount. The comparison unit 104 calculates the feature amount of sound effect based on the reduction amount.

Here, the feature amount of sound effect include sound volume, reproduction timing, a frequency, a change speed of a pan-pot, and reproduction time. Items other than those described above may be included in the feature amount.

The video data processing unit 105 generates video data of video displayed on the display device 30, based on the content information 112. The video data processing unit 105 outputs generated video data to the video data transmitting unit 106. Video data is data for displaying, for example, an actually photographed moving picture photographed by the camera, video configured with predetermined CG, video configured by combining an actually photographed moving picture with CG, and the like.

The video data transmitting unit 106 transmits video data input from the video data processing unit 105 to the display device 30.

The sound data processing unit 107 generates sound data of sound to be reproduced in the terminal 20 according to reproduction of video based on the content information 112. For example, the sound data processing unit 107 generates sound data to be reproduced along with an actually photographed moving picture, sound data for expressing the background of virtual world, and sound data of sound expressing movement of an object.

The sound data processing unit 107 generates sound data of sound effect based on the feature amount calculated by the comparison unit 104. The sound data is data into which the operation of the user is reflected. The sound data processing unit 107 outputs generated sound data to the sound data transmitting unit 108. The comparison unit 104 having a function of generating sound data may be implemented as a generation unit. In this case, the generation unit may cause the sound data transmitting unit 108 to output through the control unit 101.

The sound data transmitting unit 108 transmits sound data input from the sound data processing unit 107 to the terminal 20.

The terminal 20 includes an acceleration sensor 201, a geomagnetism sensor 202, a sensor data transmitting unit 203, a sound reproducing unit 204, and a sound data receiving unit 205.

The acceleration sensor 201 and the geomagnetism sensor 202 measure a value indicating acceleration and a direction of the terminal 20 and output sensor data including the value to the sensor data transmitting unit 203.

Although the terminal 20 includes the geomagnetism sensor 202 as a device capable of periodically resetting a measurement error of displacement of the head of the user occurring when using only the acceleration sensor 201, the terminal 20 may include other sensors such as a gyro sensor, instead of the geomagnetism sensor 202.

The sensor data transmitting unit 203 transmits sensor data input from the acceleration sensor 201 and the geomagnetism sensor 202 to the control device 10.

The sound data receiving unit 205 receives sound data transmitted by the control device 10 and outputs the sound data to the sound reproducing unit 204.

The sound reproducing unit 204 outputs sound corresponding to sound data. The sound reproducing unit 204 is considered, for example, a speaker of a headphone.

In the present embodiment, although the terminal 20 has a measurement function and a sound reproduction function, a configuration in which the two functions are included in separate apparatuses may be adopted.

The display device 30 includes a video data receiving unit 301 and a video display unit 302.

The video data receiving unit 301 receives video data transmitted by the control device 10 and outputs the video data to the video display unit 302.

The video display unit 302 outputs video corresponding to video data. In a case where the display device 30 is a projector, the video display unit 302 projects video onto a screen and in a case where the display device 30 is a monitor, the video display unit 302 display video on a monitor screen.

The video display unit 302 may adjust a size of a display surface on which video is displayed, image quality of video, or the like.

As a communication method of data between the control device 10, the terminal 20, and the display device 30, a general communication method may be used and thus, description thereof will be omitted. A wireless communication method is used as a method for data transmission and reception between the control device 10 and the terminal 20 so that a physical connection between the control device 10 and the terminal 20 by a connection line becomes unnecessary and restrictions on the operation of the user is eliminated.

FIG. 4 is a diagram illustrating an example of the adjustment information 113 of Example 1.

The adjustment information 113 is information for adjusting the feature amount of sound effect. The adjustment information 113 of the present embodiment includes information for adjusting at least any one of sound volume, reproduction timing, the frequency, the change speed of the pan-pot, and reproduction time. In FIG. 4, the adjustment information 113 which includes frequency information 400 for adjusting a frequency is indicated.

The frequency information 400 is information indicating correlation between ages and an audible frequency. The frequency information 400 includes an entry configured with an age 401 and a maximum audible frequency 402. There is a theory that change in an audible range due to aging of women is more slower than that of men and thus, the frequency information 400 may include an entry configured with age, sex, and the maximum audible frequency.

Sensitivity is different in perception depending on frequency characteristics of organs such as the external ear, the internal ear, and the cochlea and thus, it is considered that reduction effect of sickness is high in low frequencies under the same sound volume. For that reason, the frequency of sound effect can be adjusted using the frequency information 400. For example, the frequency is adjusted so that sound effect becomes non-audible sound according to ages.

The frequency information 400 illustrated in FIG. 4 is classified in units of ten-years, but may be classified in units finer than the units of ten-years. The frequency information 400 may not be tabular format data and may be an expression using ages as a variable.

Generally, a sound volume level in human hearing is also reduced accompanied by aging and thus, the adjustment information 113 may include information for adjusting sound volume. The information includes an entry configured with ages and a ratio. The ratio is set in such a way that the greater the ages, the greater the value. For example, the ratio is set to "one time" in the case of 40 s, "1.1 times" in the case of 50 s, and "1.2 times" in the case of 60 s. The information may be an entry configured with ages and sound volume.

FIG. 5 is a diagram illustrating an example of the personal information input screen of Example 1.

A personal information input screen 500 is an operation screen used for inputting individuality of the user and is displayed on the display device 30 in starting use of the sound generation device 1. The user refers to the personal information input screen 500 and inputs the value using an input device such as a keyboard, a mouse, or the like, connected to the control device 10.

The personal information input screen 500 includes a name input field 501, an age input field 502, a sex input field 503, a sickness frequency input field 504, a registration button 505, and a cancel button 506.

The name input field 501 is a field for inputting a name of the user. A field for inputting information other than the name of the user may be available as long as the user is uniquely specified by the information. For example, the name input field is considered a field for inputting an ID of the user.

The age input field 502 is a field for inputting age of the user. In the present embodiment, the pull down list indicating age classified in units of ten-years is displayed. The age input field 502 may be a filed for directly inputting a numerical value.

The sex input field 503 is a field for inputting sex of the user. In the present embodiment, a radio button for selecting any one of male and female is displayed.

The sickness frequency input field 504 is a field for inputting a value indicating tolerance for sickness of the user. In the present embodiment, a pull down list indicating sickness frequency is displayed. The pull down list includes terms of "ever-sick", "frequently sick", "sometimes sick", "not sick", and "not absolutely sick". In the present embodiment, the user refers to the sickness frequency input field 504 to select the value corresponding to a sickness tendency during viewing of video.

The sickness frequency input field 504 may be a field for inputting the value which indicates sickness frequency. For example, the user inputs values from "0" to "9" to the sickness frequency input field 504. Here, "0" indicates that the user is not absolutely sick and "9" indicates that the user is certainly sick.

The registration button 505 is an operation button for registering the values of respective input fields. In a case where the user operates the registration button 505, the control unit 101 receives the values of respective input fields through a predetermined interface and stores data associated with the values of respective input fields into the memory 102. In a case where the control device 10 manages user information storing the entry, the control device 10 registers the entry including the input values in the user information. In a case where the control unit 101 manages user information, the user may perform inputting of the values just once using the personal information input screen 500 before starting use of the sound generation device 1. Thereafter, data indicating individuality of the user is acquired from user information based on the name of the user. In a case where update of the value is needed, the control unit 101 displays the personal information input screen 500 again and receives input.

The cancel button 506 is an operation button for stopping setting of the value. In a case where the user operates the cancel button 506, the control unit 101 initializes values of respective input fields.

Tolerance for sickness may be calculated based on use history of the sound generation device 1 and transition of sickness feeling intensity.

FIG. 6 and FIG. 7 are diagrams for explaining processing executed by the control device 10 of Example 1.

First, an outline of processing executed by the control device 10 will be described. The control device 10 calculates an amount of motion by influence of visual stimulus based on movement of the user's head and movement of video in reproducing video. The exercise amount is likely to be correlated with the visually induced self-motion perception (Vection). In the following description, the amount of motion described above is also described as an oscillation amount. The control device 10 calculates sickness feeling intensity of the user based on the amount of oscillation and calculates the reduction amount based on sickness feeling intensity of the user.

First, processing for calculating sickness feeling intensity of the user will be described using FIG. 6. Processing which will be described in the following may be periodically executed during reproduction of the moving picture and may be executed in a case where an instruction of the user is received during reproduction of the moving picture.

The control device 10 acquires sensor data acquired by the acceleration sensor 201 and the geomagnetism sensor 202 of the terminal 20 (Step S601).

Specifically, the sensor data receiving unit 103 receives sensor data as head position information indicating movement of the user's head. In the present embodiment, timings (measurement interval) at which the acceleration sensor 201 and the geomagnetism sensor 202 perform measurement are set in advance. The measurement interval can be appropriately changed by the control device 10. The measurement interval is preferably short in order to minutely grasp the movement of the user's head.

The control device 10 refers to the content information 112 to calculate the moving amount of video displayed according to video data transmitted to the display device 30 (Step S602).

Specifically, the control unit 101 acquires video data from the content information 112 and calculates the moving amount of video in the same time width as the measurement interval. Video data is acquired as one piece of stimulus information relating to stimuli input to visual sense and vestibular sense.

The moving amount of video is an estimation amount used for estimating a magnitude of the stimulus input to at least any one of visual sense and vestibular sense of the user and is represented by a vector having a moving direction and a moving distance. The control unit 101 outputs the moving amount of video to the comparison unit 104. The comparison unit 104 that receives an instruction of the control unit 101 may calculate the moving amount of video.

In a case where displayed video is a two-dimensional image, the control unit 101 calculates which point of an image, which is to be displayed next, to which a pixel or an object on an image at a certain point in time is moved. The calculation method is a known method and thus, description thereof will be omitted.

The control device 10 calculates an amount of oscillation (Step S603). Specifically, processing described in the following is executed.

The comparison unit 104 calculates a moving amount of head, which is a vector having a direction and magnitude of swing of the head of the user, at the predetermined time interval using sensor data. The comparison unit 104 sets sensor data acquired first as a reference value and calculates a difference between sensor data receive thereafter and the reference value as a value indicating swing of the head.

The comparison unit 104 calculates the amount of oscillation based on the moving amount of the head and the moving amount of video. For example, the comparison unit 104 calculates a difference between the moving amount of the head and the moving amount of video as the amount of oscillation. The comparison unit 104 temporarily stores the amount of oscillation in the memory 102.

In a case where a measurement error of sensor data exists, the comparison unit 104 may calculate the amount of oscillation using an average value of the moving amounts of head for a fixed period of time and an average value of the moving amounts of video. For example, swing of the head for a period of time during which movement of video in the right and left directions is not included corresponds to natural behavior and thus, the comparison unit 104 calculates the magnitude of the amount of oscillation as "0". In a case where swing of the head indicates change greater than natural behavior in a period of time during which video continuously moved in the right and left directions, the comparison unit 104 calculates the difference between the moving amount of the head and the moving amount of video as the amount of oscillation.

In a case where the moving amount of video is a two-dimensional vector and the moving amount of the head is a three-dimensional vector, a difference between two moving amounts by using a three-dimensional vector in which a component in the depth direction of the screen is set as "0" may be taken as the moving amount of video.

The measurement value of the acceleration sensor 201 may include natural behavior (noise) irrespective of oscillation caused by viewing of video. For that reason, the noise described above may be reduced using a method of calculating the moving amount of the head by combining the measurement value of the acceleration sensor 201 and the measurement value of the geomagnetism sensor 202 and then, calculates the difference between the moving amount of the head and the moving amount of video or a method of performing frequency component analysis for the measurement value of the acceleration sensor 201 to selectively extract an amount of component in a specific frequency band close to the frequency of the screen movement within a predetermined period of time. Matters described above correspond to description of Step S603.

The control device 10 calculates sickness feeling intensity based on the amount of oscillation (Step S604).

For example, the comparison unit 104 calculates the magnitude (scalar value) of the amount of oscillation as sickness feeling intensity. The comparison unit 104 executes statistic processing to calculate a variation ratio of the temporal amount of oscillation as sickness feeling intensity. More specifically, the comparison unit 104 calculates an average value of variation ratios of respective components as sickness feeling intensity.

The control device 10 calculates the reduction amount based on sickness feeling intensity (Step S605).

Specifically, the comparison unit 104 acquires the value indicating tolerance for sickness from data (for example, entry stored in user information) indicating individuality of the user stored in the memory 102. The comparison unit 104 calculates the reduction amount based on tolerance for sickness and sickness feeling intensity and stores the reduction amount in the memory 102 through the control unit 101.

For example, the comparison unit 104 calculates the feature amount itself of sound effect as the reduction amount. In a case where an expression for determining the feature amount is given, the comparison unit 104 calculates the value correcting a coefficient of the expression or a calculation result of the expression as the reduction amount.

In a case where data indicating individuality of user does not exist in the memory 102, the comparison unit 104 executes processing using a predetermined default value.

Next, processing for reproducing sound effect will be described using FIG. 7. Processing to be described in the following is repeatedly executed during reproduction of the moving picture. An execution period can be arbitrarily set.

The control device 10 determines whether sound effect needs to be output or not (Step S701).

For example, a method in which the comparison unit 104 determines whether sound effect is to be output based on the reduction amount or not may be considered. In a case where the reduction amount is a scalar value, the comparison unit 104 determines whether the reduction amount is greater than or equal to a threshold value or not. In a case where the reduction amount is a vector, the comparison unit 104 determines whether a value of at least one component is greater than or equal to a threshold value or not or determines whether an inner product of the vector is greater than or equal to a threshold value or not. Similar determination may be performed on two or more components.

The threshold value used for the determination depends on a data bit width and accuracy of the acceleration sensor and thus, a value determined based on a test performed in advance is used. The threshold value can be appropriately changed.

In a case where it is determined that sound effect does not need to be output, the control device 10 ends processing.

In a case where it is determined that sound effect needs to be output, the control device 10 calculates the feature amount of sound effect (Step S702). Specifically, the comparison unit 104 calculates the feature amount of sound effect based on the reduction amount and stores the feature amount in the memory 102 through the control unit 101.

For example, in a case where the expression for determining the feature amount using the reduction amount is given, the comparison unit 104 calculates the feature amount based on the reduction amount and the expression and refers to the adjustment information 113 based on individuality of the user to correct the calculated feature amount. The adjustment information 113 may be used when the feature amount is calculated. For example, a method of selecting a constant to be set in the expression based on the adjustment information 113 may be considered. The comparison unit 104 stores the calculated feature amount in the memory 102.

The feature amount sound data of sound effect is corrected based on the adjustment information 113 so as to make it possible to improve reduction effect of sickness due to sound effect, reduce a burden on a user, or the like.

In a case where the feature amount itself of sound effect is calculated as the reduction amount, processing of Step S702 may be omitted.

The control device 10 determines whether another sound effect is being reproduced or not (Step S703). For example, the control device 10 manages states in starting reproduction of sound effect and in ending reproduction of sound effect so as to make it possible to determine whether another sound effect is being reproduced or not. The determination is executed by the control module 111.

In a case where it is determined that another sound effect is being reproduced, the control device 10 ends processing. In this case, data relating to the feature amount of sound effect may be discarded. After a fixed period of time elapses, determination in Step S703 may be executed again.

In a case where it is determined that another sound effect is not being reproduced, the control device 10 generates sound data of sound effect and transmits the sound data to the terminal 20 to reproduce sound effect (Step S704). Thereafter, the control device 10 ends processing.

Specifically, the control unit 101 outputs the feature amount stored in the memory 102 to the sound data processing unit 107 to instruct generation of sound data of sound effect. The sound data processing unit 107 generates sound data based on the feature amount and outputs the sound data to the sound data transmitting unit 108. The sound data transmitting unit 108 transmits the sound data to the terminal 20. The sound reproducing unit 204 of the terminal 20 reproduces sound effect based on the received sound data.

The feature amount may be calculated by taking into account reproduced video or the like. For example, in a case where sound effect is reproduced in matching with movement of video of which occurrence of motion according to the Vection is predicted, reproduction timing and reproduction speed (reproduction time) associated with video are calculated as the feature amount. In this case, the control module 111 instructs the sound data processing unit 107 to generate sound data in matching with reproduction timing. With this, auditory stimulus is given at the time of generation of motion described above so as to make it possible to comprehensively execute sickness reduction processing.

In a case where the reduction amount is changed during reproduction of sound effect, the feature amount may be corrected based on the reduction amount after the change. For example, in a case where the determination result in Step S703 is "YES", the control module 111 or the comparison unit 104 executes sound volume correction processing. In this processing, in a case where a magnitude of the reduction amount is "0", the control module 111 or the comparison unit 104 corrects sound volume to "0" and in a case where the magnitude of the reduction amount is greater than the maximum value of the magnitude of the past reduction amount, the control module 111 or the comparison unit 104 corrects sound volume to the maximum value. Furthermore, the control module 111 or the comparison unit 104 linearly complements sound volume before the reduction amount is changed and sound volume after the reduction amount is changed. Processing described above is an example and can be arbitrarily corrected within a range in which sickness reduction effect is obtained.

In a case where the control device 10 monitors temporal change of the reduction amount after reproduction of sound effect and a state where the reduction amount is greater than the threshold value continues for a fixed period of time, the control device 10 regards that sickness exceeding sickness reduction effect due to sound effect occurs and may reproduces a warning message indicating deterioration of a sickness state as voice or an image.

Next, sound effect will be described using FIG. 8A and FIG. 8B. FIG. 8A and FIG. 8B are diagrams illustrating an example of sound effect reproduced by the terminal 20 of Example 1. In FIG. 8A and FIG. 8B, a format of sound data to be applied to a 2-channel stereo acoustic system is illustrated. In a format of sound data of a 5.1-channel acoustic system or the like, similar sound data may be applied to left and right output channels which are main channels.

First, FIG. 8A will be described. Reproduction timing (reproduction start time) of sound effect illustrated is FIG. 8A is a point in time at which the determination result in Step S703 is determined as NO.

The terminal 20 raises sound volume of a left ear side from 0 to the maximum sound volume 61 and then, lowers the sound volume to minute sound volume 82. In this case, the terminal 20 raises sound volume of a right ear side from 0 to sound volume 63 and then, changes the sound volume of the right ear side to minute sound volume 52 so as to be synchronized with change in sound volume of the left ear side.

The terminal 20 raises sound volume of the right ear side to the maximum sound volume δ1 and then lowers the sound volume of the right ear side to 0, after sound volume of each ears is changed to the minute sound volume δ3 and a predetermined period of time elapses therefrom. In this case, the terminal 20 raises sound volume of the left ear side to δ3 and then, lowers the sound volume of the left ear side to 0 so as to be synchronized with change in sound volume of the right ear side.

The feature amounts such as reproduction timing, sound volume, and reproduction speed may be calculated based on the reduction amount at a certain point in time and may be calculated based on temporal change of the reduction amount.

The auditory stimulus is given using sound effect described above so as to make it possible for the user to perceive matters that a sound source moves from the left side to the right side and to recall feeling of movement to the left direction. The change in the sound volume in the left and right side is mutually interchanged so as to make it possible to recall feeling of movement to the right direction.

Feeling of movement in a direction opposite to the moving direction of the body of the user due to influence of the visual stimulus is caused to recall so as to make it possible to reduce oscillation of the head.

FIG. 8B illustrates a stereo binaural signal which is convolved with a head transfer function. The terminal 20 reproduces the binaural signal as sound effect (audible sound) such as white noise so as to make it possible for the user to perceive the sound effect as sound revolving in a counterclockwise direction along the time axis and recall feeling of rotation in the counterclockwise direction. The auditory stimuli of the right ear and left ear are mutually interchanged so as to make it possible for the terminal 20 to reproduce sound effect revolving in the clockwise direction.

A value of the head transfer function is stored in the memory 102 and the value is used so as to make it possible to reproduce data obtained by changing the frequency characteristics from an arbitrary sound source data as sound effect generated from an arbitrary distance in an arbitrary direction in three-dimensional space.

Sound data reproducing sound effect (non-audible sound) which does not hinder sound may be generated based on the content information 112. For example, the control device 10 generates sound data reproducing sound having a frequency of 16 KHz and waveforms as illustrated in FIG. 8A or FIG. 8B. The sound having the frequency can be perceived by a young user but not by an old user.

For oscillation of the head, oscillation in the up and down directions as well as the left and right directions may be taken into account. In this case, a sound source which generates feeling of movement of the user in the front and rear directions is used for the moving amount in the depth direction of video so as to make it possible to obtain similar effects.

According to Example 1, the sound generation device 1 gives the auditory stimulus so as to make it possible to reduce sickness of a user who views video. The sound generation device 1 can adjust sound effect in matching with individuality of the user and thus, sickness reduction effect can be improved and a burden on the user can be reduced. The auditory stimulus is not a stimulus required to cause the current or the like to flow directly and thus, a burden on a user is low. The user does not need to actively carry out an action and thus, a burden on a user is low.

The sound generation device 1 of Example 1 can be implemented using a general-purpose apparatus and device and thus, introduction costs can be suppressed low.

Example 2

Example 2 intends to reduce sickness of a user who gets on a transport apparatus such as a vehicle or a ship. In the following, description will be mainly made on a difference between Example 1 and Example 2.

It is considered that the cause of sickness occurred by the user who gets on the transport apparatus is similar to the cause of sickness which occurs in a case of viewing video. For example, in a case where the user is in reading in a state where the user who gets on the transport apparatus is seated on a seat, matters that the user remains in stationary are perceived by visual sense and matters that the user being moved accompanied by movement of the transport apparatus are perceived by vestibular sense. Accordingly, it is considered that the discrepancy between perceptions is the cause of sickness.

FIG. 9 is a diagram illustrating a configuration of the sound generation device 1 mounted on a transport apparatus 2 of Example 2.

The sound generation device 1 mounted on the transport apparatus 2 is configured with the control device 10, the terminal 20, and a first image-capturing device 50. The terminal 20 and the first image-capturing device 50 are connected with the control device 10 wirelessly or in a wired manner.

The control device 10 of Example 2 controls the entirety of an electronic device of the transport apparatus 2. Similar to the control device 10 of Example 1, the control device 10 of Example 2 controls generating and outputting of sound data of sound effect. The control device 10 of Example 2 is considered, for example, a microcomputer.

The terminal 20 of Example 2 is the same as the terminal 20 of Example 1 and thus, description thereof will be omitted. The terminal 20 of Example 2 may use an open ear type headphone to hear environment sound as well as sound effect. The same number of terminals 20 as the number of persons capable of being allowed to get on the transport apparatus 2 may exist.

The first image-capturing device 50 photographs video in an advancing direction of the transport apparatus 2. The first image-capturing device 50 may be an apparatus such as a stereo camera capable of measuring a three-dimensional shape.

FIG. 10 is a diagram illustrating an example of a hardware configuration and software configuration of the sound generation device 1 of Example 2.

The control device 10 includes the control unit 101, the memory 102, the sensor data receiving unit 103, the comparison unit 104, the sound data processing unit 107, the sound data transmitting unit 108, an acceleration sensor 121, and a data receiving unit 122.

The control device 10 may include an internal storage device such as the HDD and the SSD. The control device 10 may include a plurality of acceleration sensors 121 in consideration of a size or characteristics of the transport apparatus 2.

The control unit 101, the memory 102, the sensor data receiving unit 103, the comparison unit 104, the sound data processing unit 107, and the sound data transmitting unit 108 are the same as those included in the control device 10 of Example 1 and thus, description thereof will be omitted.

The control module 111, adjustment information 113, and user information are stored in the memory 102 of Example 2. A portion of processing executed by the comparison unit 104 of Example 2 is different from processing executed by the comparison unit 104 of Example 1.

The acceleration sensor 121 measures acceleration of the transport apparatus 2. The control device 10 may include a plurality of acceleration sensors 121 in consideration of a size or characteristics of the transport apparatus 2. In a case where only the acceleration sensor 121 is used, there is a possibility that the measurement error is accumulated and thus, the measurement error may be periodically corrected using the geomagnetism sensor, the gyro sensor, or the like.

The data receiving unit 122 receives sensor data from the acceleration sensor 121 and receives image data from the first image-capturing device 50.

The terminal 20 includes the acceleration sensor 201, the geomagnetism sensor 202, the sensor data transmitting unit 203, the sound reproducing unit 204, and the sound data receiving unit 205. Respective configurations are the same as those of Example 1 and thus, description thereof will be omitted.

FIG. 11 is a diagram for explaining processing executed by the control device 10 of Example 2. Processing to be described in the following is periodically executed during movement of the transport apparatus 2.

The control device 10 acquires sensor data acquired by the acceleration sensor 201 and the geomagnetism sensor 202 of the terminal 20 (Step S601).

The control device 10 calculates the moving amount of the transport apparatus 2 (Step S1101). Specifically, processing as in the following is executed.

The control unit 101 calculates a changed value of acceleration of the transport apparatus 2 using sensor data acquired by the acceleration sensor 121. The control unit 101 calculates a physical amount indicating change in a shape of an object included in an image based on image data acquired from the first image-capturing device 50. Sensor data acquired by the acceleration sensor 121 and the image data acquired from the first image-capturing device 50 are acquired as one piece of stimulus information relating to stimulus which is input to visual sense and vestibular sense.

The control unit 101 calculates the moving amount of the transport apparatus 2 from the changed value of acceleration and the physical amount. The moving amount is an estimation amount for estimating the magnitude of stimulus input to at least any one of visual sense and vestibular sense of the user and is represented as a vector having the moving direction and the moving distance.

In a case where the moving amount of the transport apparatus 2 is calculated, when only the value of acceleration sensor 121 is used, the moving amount of the transport apparatus 2 cannot be correctly calculated and thus, change in the image is also taken into account. For example, in a case where the transport apparatus 2 travels on the left curve of a paved road on the road, a shape of a road surface is bent in the left direction. In this case, acceleration is measured in the right direction due to centrifugal force. However, a value to be measured by the acceleration sensor 121 is changed due to the inclination of the road surface. The control unit 101 calculates the inclination of the road surface from change in image data and corrects the value measured by the acceleration sensor 121 using the calculated value.

The control unit 101 calculates the moving amount of the transport apparatus 2 at the same time width as the measurement interval. The control unit 101 sets a value of the acceleration sensor in a state where the transport apparatus 2 is stopped as a reference value and calculates the difference between received sensor data and the reference value as the changed value of acceleration.

In a case where the control device 10 includes a plurality of acceleration sensors 121, processing described above may be executed by using the average value of values measured by respective acceleration sensors 121 or an intermediate value.

In consideration of an operation state of the transport apparatus 2 such as a handle operation, an access operation, a brake operation, and a blinker operation of a vehicle, and steering of a ship, the value measured by the acceleration sensor 121 may be corrected. Matters describe above correspond to description of processing in step S1101.

The control device 10 calculates the amount of oscillation (step s1102). Specifically, processing as in the following is executed.

The comparison unit 104 calculates the moving amount of the head in a predetermined time interval using sensor data. A calculation method of the moving amount of the head is the same as Example 1 and thus, description thereof will be omitted.

The comparison unit 104 calculates the amount of oscillation based on the moving amount of the head and the moving amount of the transport apparatus 2. For example, the comparison unit 104 calculates the difference between the moving amount of the head and the moving amount of the transport apparatus 2 as the amount of oscillation. The comparison unit 104 temporarily stores the amount of oscillation in the memory 102.

In a case where the measurement error of sensor data exists, the comparison unit 104 may calculate the amount of oscillation using the average value of the moving amounts of video and the average value of the moving amounts of the head for a fixed period of time. For example, in a case where acceleration of the transport apparatus 2 in the right and left directions is less than the threshold value, swing of the head is natural behavior and thus, the comparison unit 104 calculates the magnitude of the amount of oscillation as "0". In a case where acceleration of the transport apparatus 2 in the right and left directions is greater than or equal to the threshold value for a predetermined period of time, the comparison unit 104 calculates the difference between the moving amount of the head and the moving amount of video as the amount of oscillation.

The control device 10 calculates sickness feeling intensity based on the amount of oscillation (Step S604) and calculates the reduction amount based on sickness feeling intensity (Step S605).

Processing for reproducing sound effect is the same as processing illustrated in FIG. 7 and thus, description thereof will be omitted.

Although the control device 10 of Example 1 presents a warning message indicating deterioration of a sickness state as voice or an image to the user, the control device 10 of Example 2 may present the warning message to a user who operates the transport apparatus 2, in addition to the user.

According to Example 2, the sound generation device 1 gives an auditory stimulus so as to make it possible to reduce sickness of the user who gets on the transport apparatus 2. The sound generation device 1 can adjust sound effect in matching with individuality of the user and thus, sickness reduction effect can be improved and a burden on the user can be reduced. The auditory stimulus is not a stimulus required to cause the current or the like to flow directly and thus, a burden on a user is low. The user does not need to actively carry out an action and thus, a burden on a user is low.

The sound generation device 1 of Example 2 can be implemented using a general-purpose apparatus and device and thus, introduction costs can be suppressed low.

Example 3

Example 3 intends to reduce sickness of a user who gets on a transport apparatus such as a vehicle, similar to Example 2. In Example 3, a portion of the configuration of the sound generation device 1 differs. In the following, description will be mainly made on a difference between Example 3 and Example 2.

FIG. 12 is a diagram illustrating a configuration of the sound generation device 1 mounted on the transport apparatus 2 of Example 3.

The sound generation device 1 mounted on the transport apparatus 2 is configured with the control device 10, the first image-capturing device 50, a second image-capturing device 60, and a sound output device 70. The terminal 20, the first image-capturing device 50, the second image-capturing device 60, and the sound output device 70 are connected with the control device 10 wirelessly or in a wired manner.

Wearing of the terminal 20 which is a contact type device to be worn by the user may be difficult or troublesome. The transport apparatus 2 of Example 3 is different from the transport apparatus 2 of Example 2 in that the second image-capturing device 60 and the sound output device 70 are provided, instead of the terminal 20.

The second image-capturing device 60 photographs the user. The sound output device 70 outputs sound to the user. In FIG. 12, although only one sound output device 70 is displayed, one sound output device 70 exists in right and left sides of the transport apparatus 2. The second image-capturing device 60 is considered a camera and the sound output device 70 is considered a stereo speaker. The second image-capturing device 60 and the sound output device 70 are installed only at the rear seat, but may also be installed at other seats. The movement of a plurality of users may be detected by using one second image-capturing device 60.

Other configurations of the transport apparatus 2 of Example 3 are the same as those of the transport apparatus 2 of Example 2 and thus, description thereof will be omitted.

FIG. 13 is a diagram illustrating an example of a hardware configuration and software configuration of the sound generation device 1 of Example 3.

The control device 10 includes the control unit 101, the memory 102, the comparison unit 104, the sound data processing unit 107, the sound data transmitting unit 108, the acceleration sensor 121, and the data receiving unit 122. The control device 10 may include the internal storage device such as the HDD and the SSD.

The control unit 101, the memory 102, the comparison unit 104, the sound data processing unit 107, the sound data transmitting unit 108, the acceleration sensor 121, and the data receiving unit 122 are the same as those included in the control device 10 of Example 2 and thus, description thereof will be omitted. The data receiving unit 122 receives image data from each of the first image-capturing device 50 and the second image-capturing device 60.

The sound output device 70 includes the sound data receiving unit 205 and the sound reproducing unit 204. The sound data receiving unit 205 and the sound reproducing unit 204 are the same as those included in the terminal 20 of Example 2 and thus, description thereof will be omitted.

FIG. 14 is a diagram for explaining processing executed by the control device 10 of Example 3. Processing to be described in the following is periodically executed during movement of the transport apparatus 2.

The control device 10 acquires image data acquired by the second image-capturing device 60 (Step S1401). In Example 3, the image data is acquired as head position information indicating movement of the user's head. The control device 10 calculates the moving amount of the transport apparatus 2 (Step S1101).

The control device 10 calculates the amount of oscillation (Step S1402). Specifically, processing as in the following is executed.

The comparison unit 104 calculates the moving amount of the head using image data acquired from the second image-capturing device 60. A calculation method of the moving amount of the head is the same as the calculation method of the moving amount of the image of Example 1 and thus, description thereof will be omitted.

The comparison unit 104 calculates the amount of oscillation based on the moving amount of the head and the moving amount of the transport apparatus 2. For example, the comparison unit 104 calculates the difference between the moving amount of the head and the moving amount of the transport apparatus 2 as the amount of oscillation. The comparison unit 104 temporarily stores the amount of oscillation in the memory 102.

In a case where the second image-capturing device 60 is a monocular camera, two-dimensional image data is acquired and thus, the moving amount of the head becomes a two-dimensional vector, and in a case where the second image-capturing device 60 is a stereo camera or an infrared camera, three-dimensional image data is acquired and thus, the moving amount of the head becomes a three-dimensional vector.

The control device 10 calculates sickness feeling intensity based on the amount of oscillation (Step S604) and calculates the reduction amount based on sickness feeling intensity (Step S605).

Processing for reproducing sound effect are the same as processing illustrated in FIG. 7 and thus, description thereof will be omitted. However, in Step S704, voice or character information explaining the sound effect is output before reproduction of sound effect.

Similar to Example 2, the control device 10 of Example 3 may present the warning message to a user who operates the transport apparatus 2, in addition to the user.

According to Example 3, it is possible to obtain the same effect as Example 2 without using a wearable device.

The present invention is not limited to the embodiments described above and includes various modification examples. For example, the embodiments described above are described in detail in order to make it easy to understand the present invention and the present invention is not necessarily limited to the embodiment provided with all configurations described above. A portion of the configuration of each embodiment may be added to, deleted from, and replaced with another configuration.

Some or all of configurations, functions, processing units, processing means, and the like described above may be implemented by hardware, for example, by designing those with an integrated circuit. The present invention can also be implemented by a program code of software implementing the functions of the embodiments. In this case, a non-temporary storage medium having stored the program code is provided to a computer and a processor included in the computer reads the program code stored in the non-temporary storage medium. In this case, the program code itself read out from the non-temporary storage medium implements the functions of the embodiments described above and the program code itself and the non-temporary storage medium having stored the program code configure the present invention. As a storage medium for supplying such program code, for example, a flexible disk, a CD-ROM, a DVD-ROM, a hard disk, a solid state drive (SSD), an optical disk, a magneto-optical disk, a CD-R, a magnetic disk, a non-volatile memory card, and a ROM are used.

A program code that realizes the function described in the present embodiment can be implemented in a broad range of programming languages and script languages, for example, Assembler, C/C++, perl, Shell, PHP, Java (registered trademarks).

Furthermore, the program code of software implementing the functions of the embodiments may be distributed through a network to store the program code in a storage unit such as the hard disk or the memory of the computer or a storage medium such as the CD-RW or the CD-R and to cause the processor included in the computer to read the program code stored in the storage unit or the storage medium to be executed.

In the embodiment described above, control lines and information lines, which are considered necessary for explanation, are illustrated and those lines do not necessarily illustrate all of control lines and information lines needed for a product. All configurations may be connected with each other.

REFERENCE SIGNS LIST

1: sound generation device
2: transport apparatus
10: control device
20: terminal
30: display device
50: first image-capturing device
60: second image-capturing device
70: sound output device
101: control unit
102: memory
103: sensor data receiving unit
104: comparison unit
105: video data processing unit
106: video data transmitting unit
107: sound data processing unit
108: sound data transmitting unit
111: control module
112: content information
113: adjustment information
121, 201: acceleration sensor
122: data receiving unit
202: geomagnetism sensor
203: sensor data transmitting unit
204: sound reproducing unit
205: sound data receiving unit
301: video data receiving unit
302: video display unit

The invention claimed is:

1. An apparatus that reduces sickness of a user, comprising:
a first acquisition unit that acquires head position information indicating movement of a head of the user;
a second acquisition unit that acquires stimulus information relating to a stimulus input to a visual sense and a vestibular sense; and
a generation unit that generates sound data of sound effect generating movement of a body which reduces sickness based on the head position information and the stimulus information,
wherein the generation unit
calculates a variation amount of a position of a head of the user based on the head position information,
calculates an estimation amount for estimating a magnitude of the stimulus input to at least any one of the visual sense and the vestibular sense based on the stimulus information,
calculates sickness feeling intensity indicating intensity of sickness feeling of the user based on the variation amount of the position of the head of the user and the estimation amount,
calculates a reduction amount based on the sickness feeling intensity,
determines whether the reduction amount is greater than or equal to a threshold,
when the reduction amount is greater than or equal to the threshold, calculate a feature amount of sound data based on the reduction amount to generate the sound effect,
determine whether a second sound is being produced, and
when the second sound is not being produced outputs the sound effect based on the calculated feature amount.

2. The apparatus according to claim 1,
wherein the apparatus holds adjustment information for correcting the sound data based on individuality of the user, and
the generation unit
acquires data indicating individuality of a targeted user,
corrects the feature amount of the sound data by referring to the adjustment information based on the data indicating individuality of the targeted user, and
generates the sound effect based on the feature amount of the corrected sound data.

3. The apparatus according to claim 2,
wherein the first acquisition unit acquires the head position information of a user who views video displayed on a display device,
the second acquisition unit acquires video data displaying the video, and
the generation unit calculates a moving amount of the video as the estimation amount based on the video data.

4. The apparatus according to claim 2,
wherein the first acquisition unit acquires the head position information of a user who gets on a transport apparatus,
the second acquisition unit acquires data indicating movement of the transport apparatus, and
the generation unit calculates a moving amount of the transport apparatus as the estimation amount based on the data indicating movement of the transport apparatus.

5. The apparatus according to claim 2,
wherein the feature amount of the sound data is at least any one of sound volume, a frequency, reproduction timing, and reproduction time.

6. The apparatus according to claim 2,
wherein the apparatus is connected to a sound output device reproducing the sound effect based on the sound data,
in a case where the sound data is to be output to the sound output device, it is determined whether or not the sound output device reproduces the sound effect, and
in a case where it is determined that the sound output device does not reproduce the sound effect, the sound data is output to the sound output device.

7. A sound data generation method executed by an apparatus that generates sound data of sound effect reducing sickness of a user, the apparatus including an operation device and a storage device connected to the operation device, the method comprising;
a first step of acquiring head position information indicating movement of a head of the user, by the operation device;
a second step of acquiring stimulus information relating to a stimulus input to a visual sense and a vestibular sense, by the operation device;
a third step of calculating a variation amount of a position of a head of the user based on the head position information, by the operation device;
a fourth step of calculating an estimation amount for estimating a magnitude of the stimulus input to at least any one of the visual sense and the vestibular sense based on the stimulus information, by the operation device;

a fifth step of calculating sickness feeling intensity indicating intensity of sickness feeling of the user based on the variation amount of the position of the head of the user and the estimation amount, by the operation device;

a sixth step of calculating a reduction amount based on the sickness feeling intensity, by the operation device;

a seventh step of determining whether the reduction amount is greater than or equal to a threshold, by the operation device in a case where the reduction amount is greater than or equal to the threshold, calculating a feature amount of sound data based on the reduction amount to generate the sound data, by the operation device; and an eighth step of determining whether a second sound is being produced; and in a case where the second sound is not being produced output a sound effect based on the calculated feature amount.

8. The sound data generation method according to claim 7, wherein the apparatus holds adjustment information for correcting the sound data based on individuality of the user, the sixth step includes a step of acquiring data indicating individuality of a targeted user, by the operation device, and a step of correcting the feature amount of the sound data by referring to the adjustment information based on the data indicating individuality of the targeted user, in the operation device, and in the eighth step, the sound effect is generated, based on the feature amount of the corrected sound data, by the operation device.

9. The sound data generation method according to claim 8, wherein, in the first step, the head position information of a user who views video displayed on a display device is acquired by the operation device, in the second step, video data displaying the video is acquired by the operation device, and in the fifth step, a moving amount of the video is calculated as the estimation amount, based on the video data, by the operation device.

10. The sound data generation method according to claim 8, wherein, in the first step, the head position information of a user who gets on a transport apparatus is acquired by the operation device, in the second step, data indicating movement of the transport apparatus is acquired by the operation device, in the fifth step, a moving amount of the transport apparatus is calculated as the estimation amount, based on the data indicating movement of the transport apparatus, by the operation device.

11. The sound data generation method according to claim 8, wherein the feature amount of the sound data is at least any one of sound volume, a frequency, reproduction timing, and reproduction time.

12. The sound data generation method according to claim 8, wherein the apparatus is connected to a sound output device reproducing the sound effect based on the sound data, the sound data generation method comprises;

a step of determining whether or not the sound output device reproduces the sound effect, by the operation device, in a case where the sound data is to be output to the sound output device, and a step of outputting the sound data to the sound output device, by the operation device, in a case where it is determined that the sound output device does not reproduce the sound effect.

13. A non-transitory computer readable storage medium having stored thereon a program which is executed by an apparatus that generates sound data of sound effect reducing sickness of a user, the apparatus including an operation device and a storage device connected to the operation device, the program causing the apparatus to execute:

a first procedural sequence of acquiring head position information indicating movement of a head of the user;

a second procedural sequence of acquiring stimulus information relating to a stimulus input to a visual sense and a vestibular sense;

a third procedural sequence of calculating a variation amount of a position of a head of the user based on the head position information;

a fourth procedural sequence of calculating an estimation amount for estimating a magnitude of the stimulus input to at least any one of the visual sense and the vestibular sense based on the stimulus information;

a fifth procedural sequence of calculating sickness feeling intensity indicating intensity of sickness feeling of the user based on the variation amount of the position of the head of the user and the estimation amount;

a sixth procedural sequence of calculating a reduction amount based on the sickness feeling intensity; and a seventh procedural sequence of determining whether the reduction amount is greater than or equal to a threshold, when the reduction amount is greater than or equal to the threshold, calculating a feature amount of the sound data based on the reduction amount to generate the sound data; and an eighth procedural sequence of determining whether a second sound is being produced, and when the second sound is not being produced output a sound effect based on the calculated feature amount.

14. The non-transitory computer readable storage medium according to claim 13, wherein the feature amount of the sound data is at least any one of sound volume, a frequency, reproduction timing, and reproduction time, the apparatus holds adjustment information for correcting the sound data based on individuality of the user, the sixth procedural sequence includes a procedural sequence of acquiring data indicating individuality of a targeted user, and a procedural sequence of correcting the feature amount of the sound data by referring to the adjustment information based on the data indicating individuality of the targeted user, and the seventh procedural sequence includes a procedural sequence of causing the apparatus to generate the sound effect based on the feature amount of the corrected sound data.

15. The non-transitory computer readable storage medium according to claim 14, wherein the apparatus is connected to a sound output device reproducing the sound effect based on the sound data, and the program causes the apparatus to execute
a procedural sequence of determining whether or not the sound output device reproduces the sound effect in a case where the sound data is to be output to the sound output device, and
a procedural sequence of outputting the sound data to the sound output device in a case where it is determined that the sound output device does not reproduce the sound effect.

* * * * *